DENTAL ANCHORING FOR ATTACHMENT OF DENTAL PROSTHESES TO CROWNS, PIVOT TEETH, BRIDGES, AND SPLINT ELEMENTS

The invention concerns a T-attachment, characterized by a patrix mounted in a groove formed in the remainder of the teeth, with a T-profile in dovetail form, as well as a matrix cast into a removable dental prosthesis of metal.

The removable dental prosthesis basically consists of a metal plate worn in part dentally or gingivally. T-Attachments in the conventional shape serve as connecting elements between the remainder of the teeth and the removable prosthesis. Their task is to avoid the heretofore utilized, visible clamps and simultaneously to promote secure seating as well as attachment of dentures in the remainder of the teeth.

The known kind of T-attachments of the abovementioned type is no longer satisfactory for the metals, noble or base, utilized nowadays. One differentiates among three types of heretofore manufactured T-attachments: those which only consist of metal parts, those consisting of a synthetic resin and molded by the casting method by fusion of the synthetic resin parts, and those combined of a synthetic resin and a metal. All of these types have the disadvantage that they either become too expensive due to use of metal, or do not lead to the desired result by the use of molded plastic, even with maximum working accuracy, since by the fusion of the synthetic resin in the casting mold there is not obtained the hoped-for, smooth surface of the contacting parts of patrix and matrix. Even in case of T-attachments wherein a part is of metal, the remainder being supplemented by synthetic resin, the hoped-for results were not achieved, since there are no uniform, homogeneous surfaces, either, of the mutually contacting components.

This problem has been solved by the invention of the features disclosed in the claims, since, in this type of T-attachments, no limitation of any kind is encountered. By the special configuration of the patrix and matrix, all contact surfaces are stamped from thin-gage embossing material and therefore are, firstly, economical with a favorable price and provide inexpensive processing, since neither the patrix nor the matrix require finishing work. In this connection, all metals presently on the market and used in casting processes can be utilized without restriction. By the shaping of this T-attachment, it has become possible for the first time to cast the crown or bridge elements directly by the integral casting provess together with the removable prosthesis part. There is great interest in this possibility, since a process of this type is increasingly desirable for economical reasons in order to obtain a uniform group of metals between the supporting elements and the removable prosthesis part.

Cumbersome soldering processes are eliminated since by the direct casting in the model casting process is rendered superfluous.

The invention is described and depicted in the dependent claims. The drawings of 8 figures represent the embodiment of the invention and will be described below.

Figure 1:
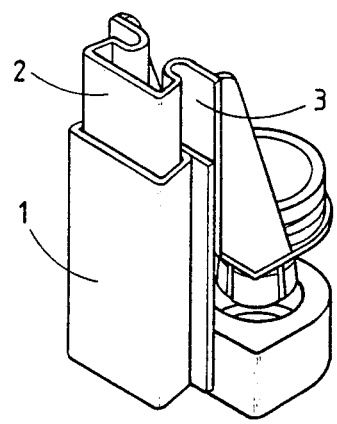
FIG. 1 shows, on an enlarged scale, patrix and matrix in half-composed disposition, the view being from the patrix side.
Figure 2:
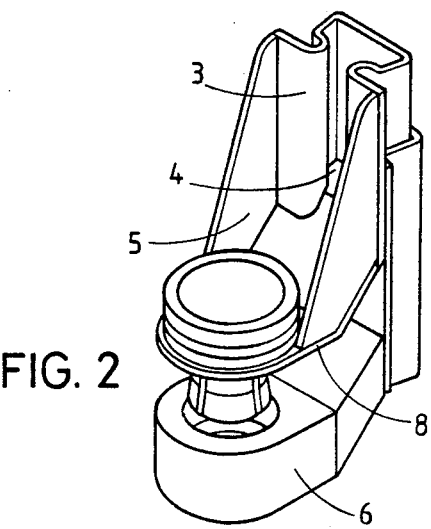
FIG. 2 shows, on an enlarged scale, patrix and matrix in half-composed disposition, the view being from the matrix side.
Figure 3:
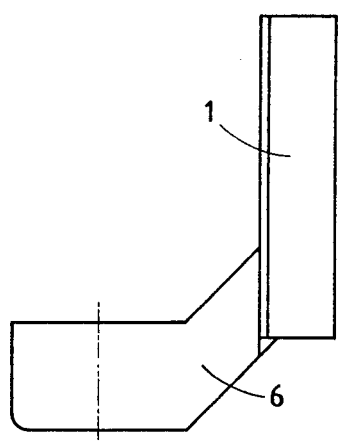
FIG. 3 is a lateral view of the patrix.
Figure 4:
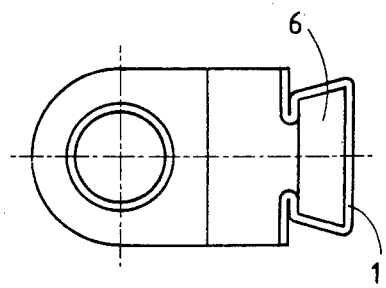
FIG. 4 is a top view of the matrix.
Figure 5:
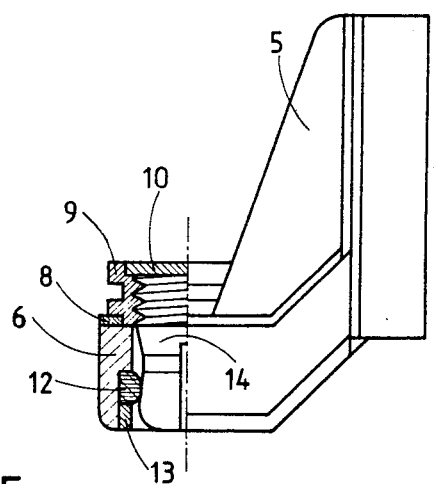
FIG. 5 is a lateral view of the combined matrix and patrix.
Figure 6:
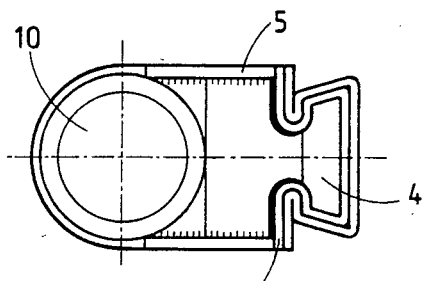
FIG. 6 is a top view of the combined matrix and patrix.
Figure 7:
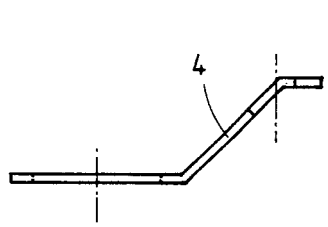
FIG. 7 is a lateral view of the lower cover of the matrix.
Figure 8:
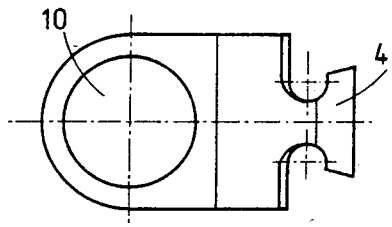
FIG. 8 is a top view of the lower cover of the matrix.

Referring now to the drawings in greater detail, there is shown a dental anchor for attachment of dental prostheses to crowns, pivot teeth, bridges, and splint elements, in the form of a T-attachment in dove tail form comprising a patrix 1 adapted to be mounted the remainder of the teeth. The patrix 1 carries a matrix 2 which does not have any internal core but rather consists of a shell form 3, having bottom wall 4 and side walls 5, making it possible, in the manufacture of the removable prosthesis by a casting method, to establish connection between the matrix 2 and the prostheses by filling the shell form 3 with casting material. The patrix 1 as well as the matrix 2 are punched out of thin-gauge sheet metal and slide into each other. The metal can be platinum-iridium or nickelchromium.

The patrix 1 is closed on its longitudinal axis by reinforced base section 6, which is angled twice about transverse axes and comprises first mounting means 12, 13. Matrix 2 has at its lower end a cover 8 which is angled about two transverse axes and which carries second mounting means 9, 10, 14 by which it is detachably secured to base 6.

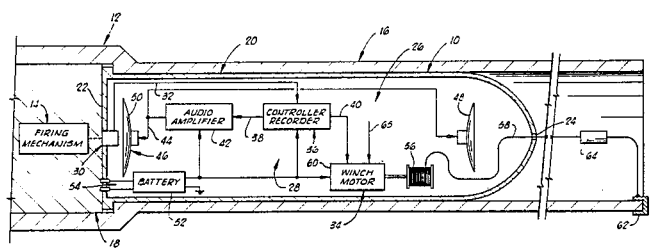

I claim:

1. In a dental device for removably supporting an artificial tooth, comprising a T-attachment in dovetail form having a patrix (1) mounted in a groove formed in the remainder of the teeth; the improvement comprising a matrix (2) having a hollow outer vertical extension serving on the one side as a slide for slidably arranging said matrix in said patrix, and on the other side as a partial female mold for the cast prosthesis, whereby said matrix and prosthesis form a removable unit and whereby said prosthesis and said remainder of the teeth can be positioned in interfitted relation.

2. A device according to claim 1, characterized in that the patrix (1) as well as the matrix (2) are punched out of thin-gage sheet metal.

3. A device according to claim 1, characterized in that the matrix (2) as well as the patrix (1) are made from platinum-iridium or nickel-chromium.

4. A device according to claim 1, characterized in that the patrix (1) as well as the matrix (2) are slidable relative to each other on mutual contact surfaces.

5. A device according to claim 1, characterized in that the patrix (1) is closed on its longitudinal axis by a reinforced base section (6).

6. A device according to claim 5, characterized in that the base section (6) is angled twice transversely of the patrix and comprises first mounting means (12, 13) co-operating with second mounting means (9, 10, 14) of said matrix detachably to secure said patrix and matrix in fixed relation.

7. A device according to claim 1, characterized in that the matrix (2) has at its lower end a base which is angled twice transversely of the matrix and supports said second mounting means (9, 10, 14) and rests on said

United States Patent [19]

Freeny, Jr. et al.

[11] Patent Number: 4,561,848
[45] Date of Patent: Dec. 31, 1985

[54] ELECTRONIC AMMUNITION FOR SIMULATING LIVE AMMUNITION DETONATION

[75] Inventors: Charles C. Freeny, Jr., Fort Worth; Ronald J. Rabin, Mansfield, both of Tex.

[73] Assignee: Power Technology Partners, Ltd., Oklahoma City, Okla.

[21] Appl. No.: 528,143

[22] Filed: Aug. 31, 1983

[51] Int. Cl.$^4$ .............................................. F41F 27/00
[52] U.S. Cl. ....................................... 434/18; 102/529
[58] Field of Search ........................ 434/16, 18, 19, 48, 434/11; 273/310-313; 102/529, 444, 501, 374, 376, 430, 473, 498; 272/14

[56] References Cited

U.S. PATENT DOCUMENTS

| | | | |
|---|---|---|---|
| 4,023,078 | 5/1977 | Olliges et al. | 434/48 |
| 4,302,190 | 11/1981 | Shaw et al. | 434/18 |
| 4,365,439 | 12/1982 | Litynski | 273/310 |

FOREIGN PATENT DOCUMENTS 2445505  8/1980  France ................................ 273/310

Primary Examiner—Richard C. Pinkham
Assistant Examiner—Leo P. Picard
Attorney, Agent, or Firm—Dunlap, Codding & Peterson

[57] ABSTRACT

The present invention contemplates electronic ammunition for simulating live ammunition detonation when utilized with an ammunition firing device having a mechanism for firing ammunition when triggered wherein an electronic sound assembly is disposed within a component space within a shell and the shell is loaded within the ammunition firing device. The electronic sound assembly has recorded therein the sound of the detonation of live ammunition and is adapted for providing the live ammunition sound in an audibly perceivable form in a play mode in response to receiving a triggered signal. The electronic ammunition includes a firing assembly which has a portion which is engagable with the firing mechanism of the ammunition firing device so that, when the electronic ammunition is loaded into the ammunition firing device and when the ammunition firing device is triggered, the triggering of the firing assembly causes the firing assembly to produce the triggered signal which is received by the electronic sound assembly and, in response to receiving the triggered signal, the electronic sound assembly is conditioned in the play mode for providing the live ammunition sound in an audibly perceivable form. The electronic ammunition of the present invention also contemplates a recoil assembly being included as a portion of the electronic ammunition and the recoil assembly is adapted to impart a simulated recoil action to the ammunition firing device in response to receiving the triggered signal.

12 Claims, 1 Drawing Figure